US011147595B2

(12) United States Patent
Finn et al.

(10) Patent No.: US 11,147,595 B2
(45) Date of Patent: Oct. 19, 2021

(54) OCCIPITAL PLATE WITH ANGLED SCREW OPENING

(71) Applicant: K2M, Inc., Leesburg, VA (US)

(72) Inventors: Michael Finn, Aurora, CO (US); Khaled Kebaish, Baltimore, MD (US); Peter Newton, La Jolla, CA (US); Harry Shufflebarger, Jupiter, FL (US); Joel Toretti, State College, PA (US); Theo Choi, Arlington, VA (US); Stacy Hollins, New Castle, VA (US); Keenan O'Brien, Grimesland, NC (US)

(73) Assignee: K2M, Inc., Leesburg, VA (US)

( * ) Notice: Subject to any disclaimer, the term of this patent is extended or adjusted under 35 U.S.C. 154(b) by 125 days.

(21) Appl. No.: 16/657,711

(22) Filed: Oct. 18, 2019

(65) Prior Publication Data
US 2020/0121370 A1    Apr. 23, 2020

Related U.S. Application Data

(60) Provisional application No. 62/747,756, filed on Oct. 19, 2018.

(51) Int. Cl.
A61B 17/70    (2006.01)
A61B 17/86    (2006.01)
A61B 17/56    (2006.01)

(52) U.S. Cl.
CPC ...... A61B 17/7044 (2013.01); A61B 17/7011 (2013.01); A61B 17/7035 (2013.01);
(Continued)

(58) Field of Classification Search
CPC ............ A61B 17/7044; A61B 17/7011; A61B 17/7035; A61B 17/7043; A61B 17/7058;
(Continued)

(56) References Cited

U.S. PATENT DOCUMENTS 10,465,459 B2 * 11/2019 Robichaux .............. E21B 33/03
2008/0051783 A1 *  2/2008 Null .................... A61B 17/7055
606/261
(Continued)

OTHER PUBLICATIONS

Extended European Search Report including the Written Opinion for Application No. EP 19020592.2 dated Apr. 23, 2020, 9 pages.

Primary Examiner — Pedro Philogene
(74) Attorney, Agent, or Firm — Lerner, David, Littenberg, Krumholz & Mentlik, LLP

(57) ABSTRACT

A surgical implant includes a first portion and a second portion. The first portion includes a body and connector assemblies. The body includes a posterior surface and defines a first bore defining an acute angle with respect to a first axis that is orthogonal to the posterior surface. The connector assemblies are disposed on opposing lateral sides of the body. Each connector assembly is selectively rotatable relative to the body. The second portion includes a base extending in a cephalad direction from the first portion, and an extension extending in the cephalad direction from the base. The base defines second bores configured to receive respective bone screws. The extension defines a third bore. The first bore of the body and the third bore of the extension define a second axis. The second bores are defined along a third axis orthogonal to the second axis.

19 Claims, 5 Drawing Sheets

(52) U.S. Cl.
CPC ...... *A61B 17/7043* (2013.01); *A61B 17/7058* (2013.01); *A61B 17/8665* (2013.01); *A61B 2017/564* (2013.01)

(58) Field of Classification Search
CPC ............ A61B 17/8665; A61B 17/7052; A61B 17/705; A61B 17/7034; A61B 17/70; A61B 17/7037; A61B 17/7055; A61B 17/8085; A61B 17/8023; A61B 17/7059; A61B 2017/00526; A61B 2017/564
See application file for complete search history.

(56) References Cited

U.S. PATENT DOCUMENTS

| | | | | |
|---|---|---|---|---|
| 2010/0094351 | A1* | 4/2010 | Haggenmaker | A61B 17/7044 606/286 |
| 2010/0222779 | A1* | 9/2010 | Ziemek | A61B 17/8042 606/71 |
| 2010/0324557 | A1* | 12/2010 | Cheema | A61B 17/7055 606/70 |
| 2014/0228891 | A1* | 8/2014 | Hammer | A61B 17/7043 606/278 |
| 2017/0290608 | A1* | 10/2017 | Neal | A61B 17/7052 |

* cited by examiner

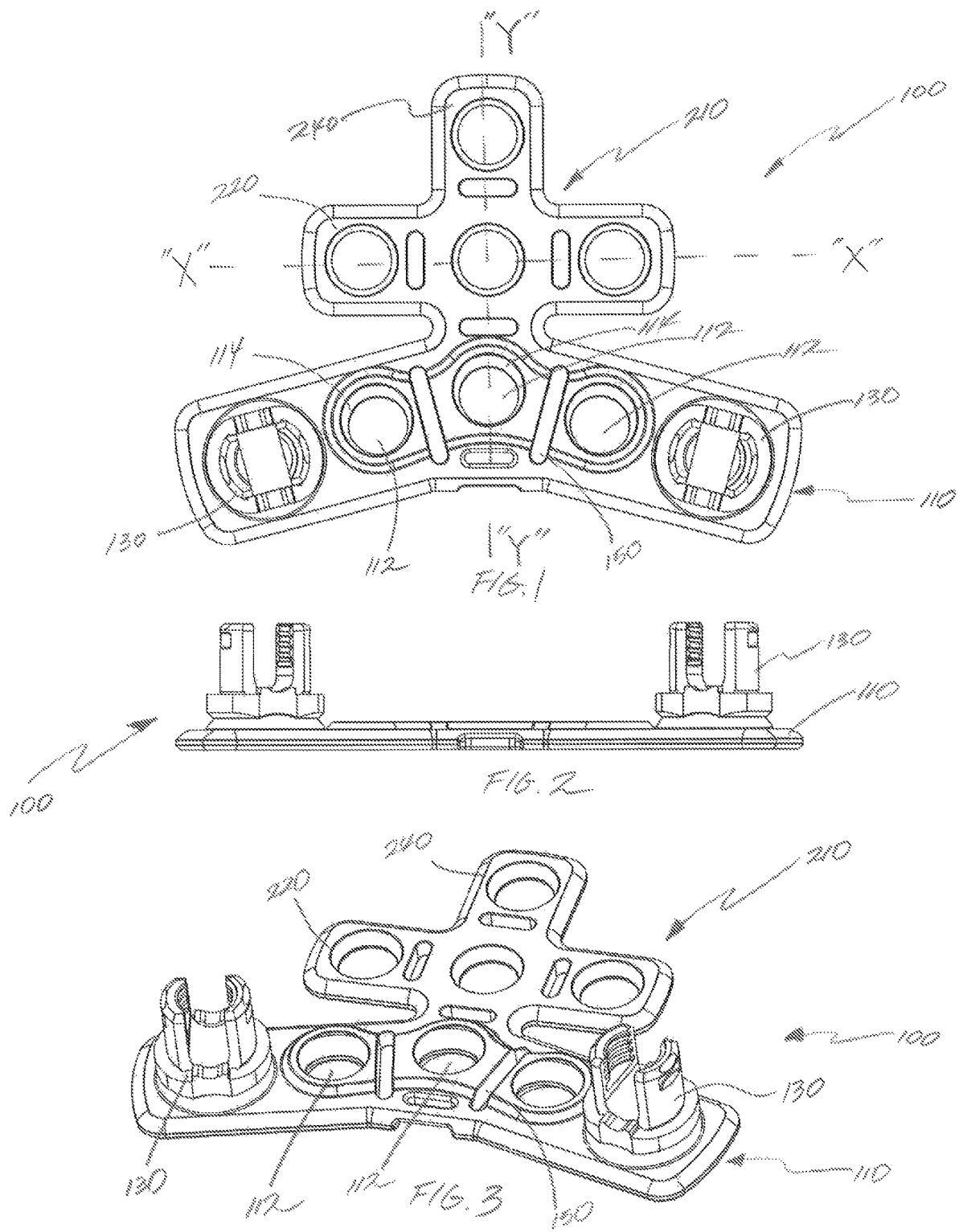

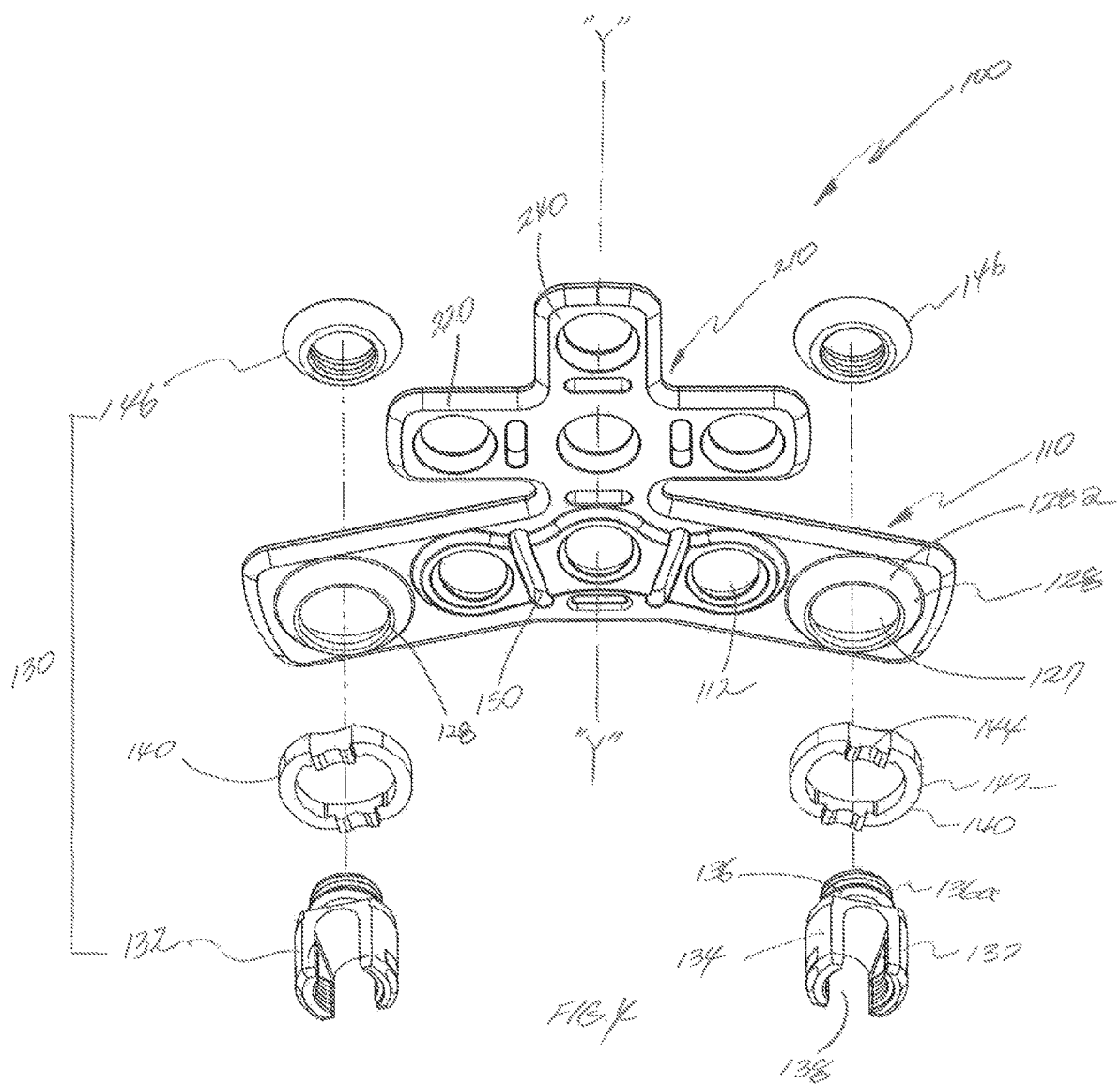

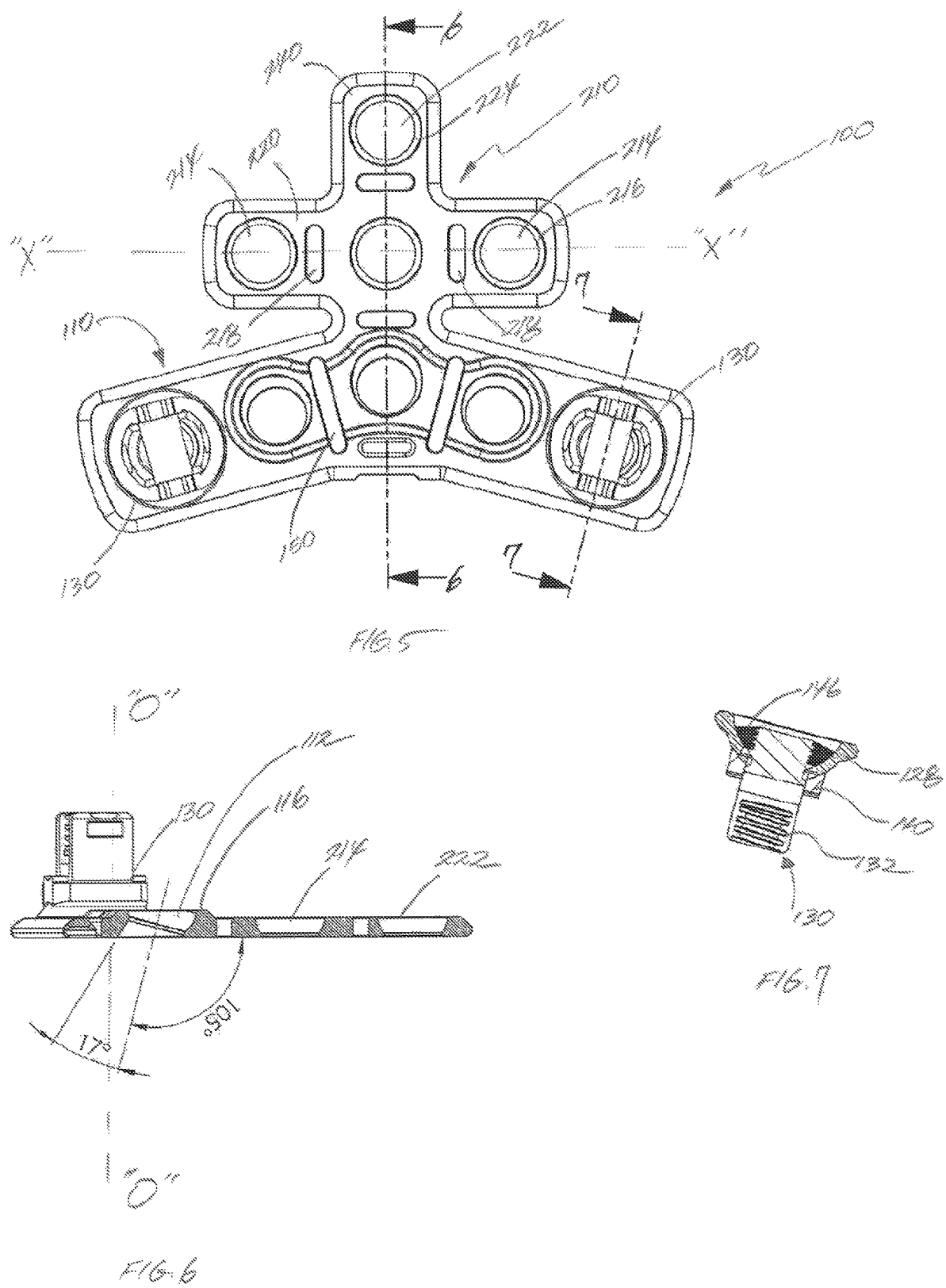

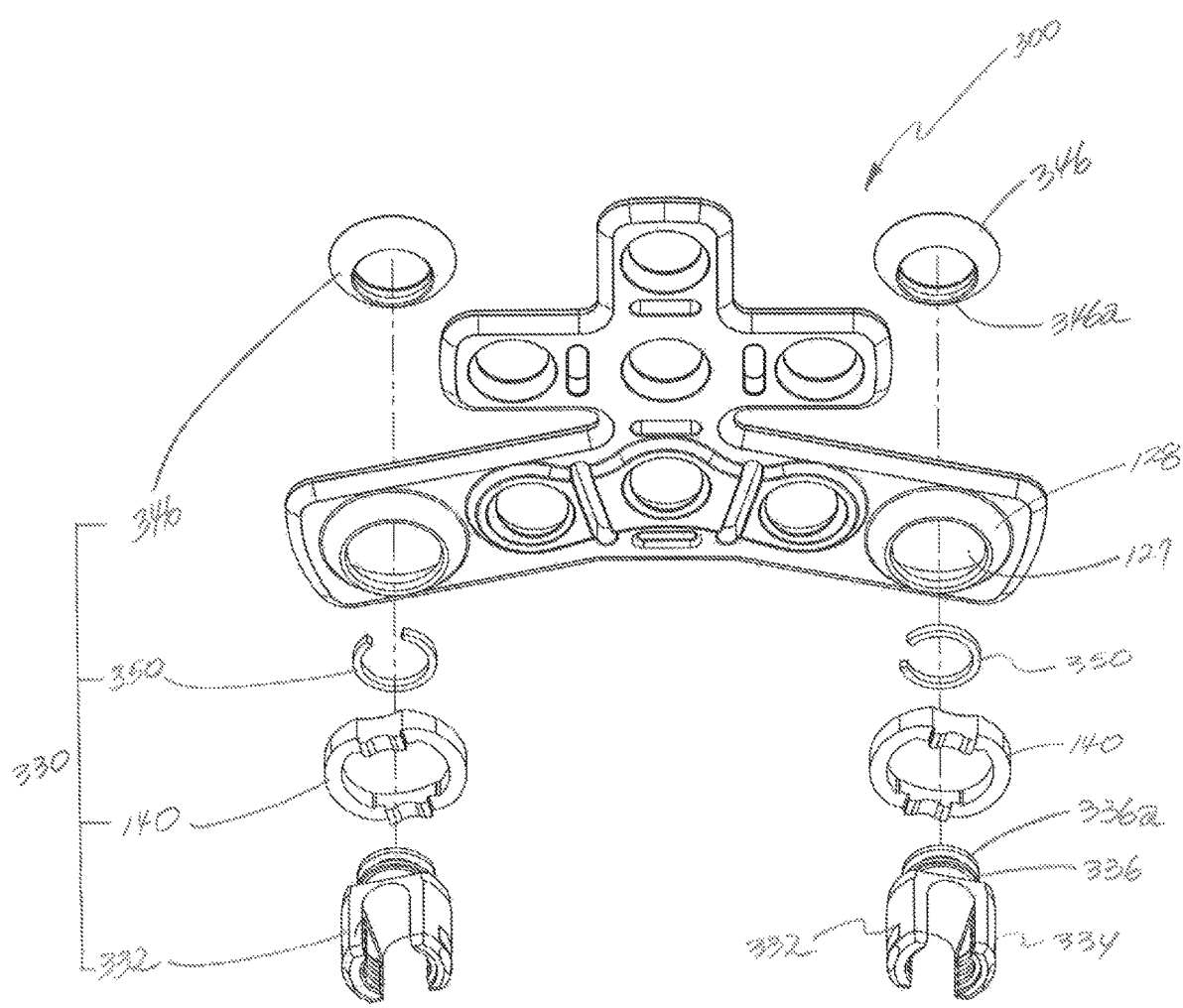

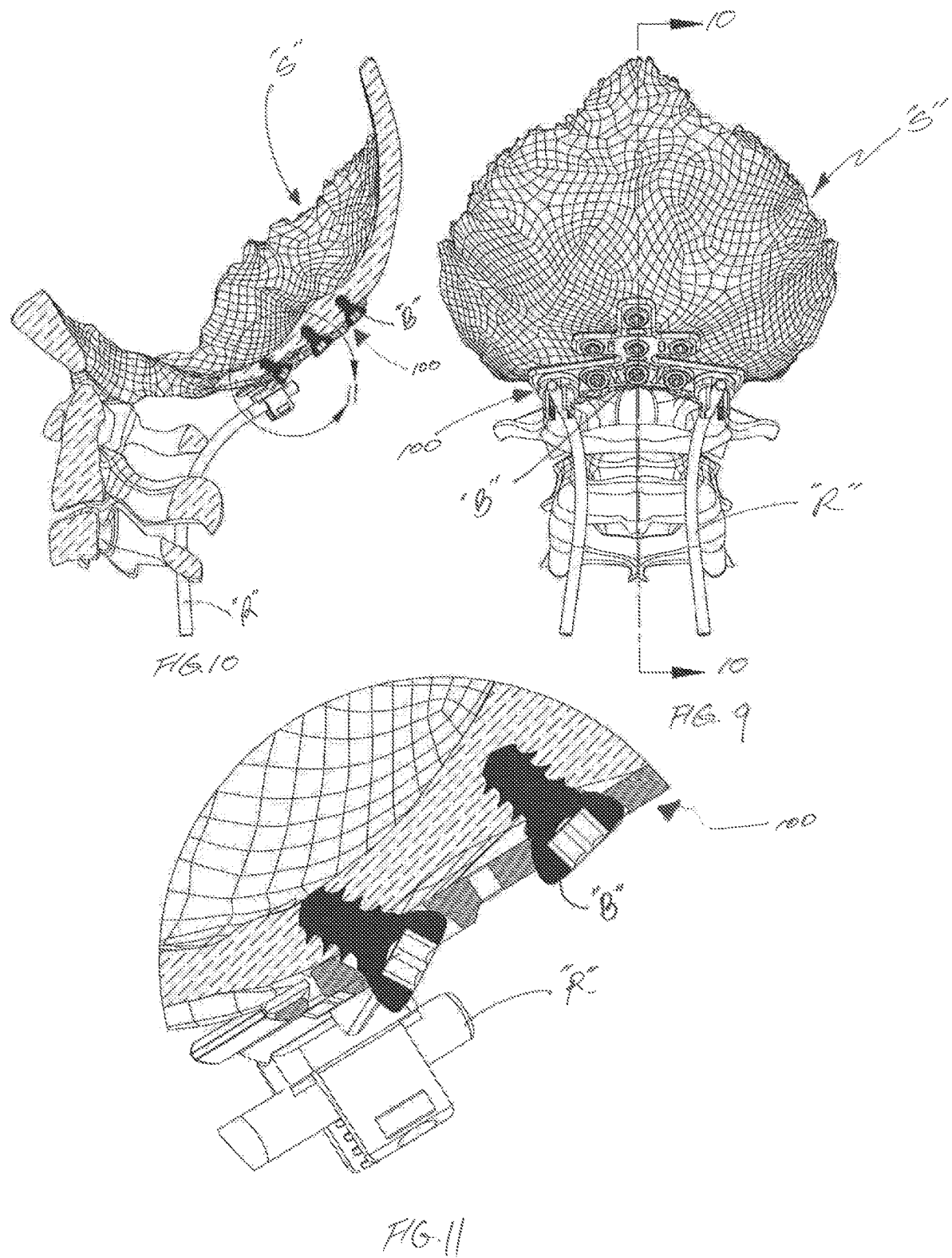

OCCIPITAL PLATE WITH ANGLED SCREW OPENING

CROSS-REFERENCE TO RELATED APPLICATIONS

This application claims the benefit of the filing date of U.S. Provisional Patent Application No. 62/747,756 filed Oct. 19, 2018, the disclosure of which is hereby incorporated herein by reference.

BACKGROUND

Technical Field

The present disclosure relates to devices for bone fixation and, more particularly, to an occipital plate for cervical fixation.

Background

The occipito-cervical junction, which comprises the occiput, atlas, and axis, represents a unique and complex interface between the cranium and the rostral cervical spine. More than 50% of the rotation and flexion-extension of the head and neck occurs in that region. In addition, the osseous articulations and their ligamentous support structures must resist force in eight axes of rotation. These include flexion, extension, bilateral lateral bending, bilateral rotation, distraction, and axial loading. Any surgical implants designed for use in this region must, therefore, have adequate dimensions to interface with the osseous structures of the spinal structures as well as have sufficient rigidity and purchase to resist these forces until bone fusion can occur. Great flexibility must be afforded to allow for the multiple anatomical variations seen in this region.

In the early 1900's occipitocervical instability and lesions located at the occipitocervical junction were considered inoperable and terminal. Since the first description of an occipitocervical fusion by Forrester in 1927, multiple methods of fusion in this region have been described. Simple onlay bone grafts with halo immobilization; wire, pin, or hook constructs; rigid metallic loops and rectangles fixed to the bone with either screws or wires; and most recently, plate or rod constructs with screws have all been described. In general, the evolution of this technology has focused on providing increasingly more rigid constructs to facilitate bone fusion and to minimize the need for and duration of external immobilization.

A common technique for fixing occipitocervical instability is the use of an inverted Y-shaped screw plate. Using this technique, the plate is secured to C1-C2 with transarticular screws and to the suboccipital bone with paramedian screws. Therefore, a need exists for a simple and effective occipital plate for cervical fixation.

SUMMARY

In accordance with an embodiment of the present disclosure, a surgical implant includes a first portion and a second portion. The first portion includes a body and connector assemblies. The body includes a posterior surface and defines a first bore defining an acute angle with respect to a first axis orthogonal to the posterior surface. The connector assemblies are disposed on opposing lateral sides of the body. Each connector assembly is selectively rotatable relative to the body. The second portion includes a base extending in a cephalad direction from the first portion, and an extension extending in the cephalad direction from the base. The base defines second bores configured to receive respective bone screws. The extension defines a third bore. The first bore of the body and the third bore of the extension define a second axis. The second bores are defined along a third axis orthogonal to the second axis.

In an embodiment, the acute angle defined by the first bore may be about 15 degrees.

In another embodiment, at least one of the connector assemblies may be configured for poly-axial movement.

In yet another embodiment, the at least one of the connector assemblies may be configured for poly-axial movement through a cone of about 25 degrees.

In an embodiment, the body of the first portion may include a mount defining a hole.

In an embodiment, the mount may include an engaging surface protruding radially inward of the hole.

In another embodiment, the connector assembly may include a housing defining a slot configured to receive a spinal rod, a support configured to support the housing and slidably engage the engaging surface of the mount, and a nut configured to be coupled with the housing in order to couple the housing to the mount of the body.

In yet another embodiment, the nut may be configured to threadably engage the housing of the connector assembly.

In still yet another embodiment, the connector assembly may further include a radially deflectable retaining ring. At least a portion of the radially deflectable retaining ring may be configured to extend radially outward from a first circular groove defined in the housing.

In still yet another embodiment, the nut may define a second circular groove configured to receive the at least a portion of the radially deflectable retaining ring extending radially outward from the first circular groove of the housing.

In an embodiment, the support may have an annular configuration. The support may define diametrically opposing recesses configured to receive the spinal rod.

In yet another embodiment, the body may further define fourth and fifth bores adjacent the first bore. At least one of the fourth or fifth bores may define an acute angle with respect to the first axis.

In an embodiment, at least one of the first, fourth, or fifth bores may be surrounded by a lip.

In another embodiment, the second portion may have an inverted T-shape.

In yet another embodiment, the first portion may be symmetric about the second axis.

In accordance with another aspect of the present disclosure, a method of surgery includes mounting a bone screw to a vertebra; securing a spinal rod to the bone screw; placing an occipital plate adjacent occipital region of a spine; securing the spinal rod with a connector assembly of the occipital plate; and securing the occipital plate to the occipital region of the spine. In particular, the occipital plate includes a first portion and a second portion. The first portion includes a body defining first bore defining an acute angle with respect to a first axis that is orthogonal to a surface of the body; and a connector assembly configured to receive the spinal rod. The connector assembly is disposed on a lateral side of the first portion. The second portion defines a second bore. The first and second bores are arranged along a second axis;

In an embodiment, securing the occipital plate may include mounting a bone screw to the occipital region of the spine through the first bore of the body.

In another embodiment, securing the occipital plate may include mounting the bone screw to the occipital region of the spine at an angle of about 15 degrees with respect to the first axis.

In yet another embodiment, securing the spinal rod with the connector assembly may include adjusting the connector assembly in a poly-axial direction relative to the body of the first portion.

In still yet another embodiment, securing the occipital plate may include mounting a bone screw to the occipital region of the spine through the second bore of the second portion.

BRIEF DESCRIPTION OF THE DRAWINGS

Various preferred embodiments of the presently disclosed occipital plate are described herein with reference to the drawings:

FIG. 1 is a top view of an occipital plate in accordance with an embodiment of the present disclosure;

FIG. 2 is a front view of the occipital plate of FIG. 1;

FIG. 3 is a perspective view of the occipital plate of FIG. 1;

FIG. 4 is an exploded perspective view of the occipital plate of FIG. 1 with parts separated;

FIG. 5 is a top view of the occipital plate of FIG. 1;

FIG. 6 is a cross-sectional view of the occipital plate of FIG. 5 cut along section line 6-6 of FIG. 5;

FIG. 7 is a cross-sectional view of the occipital plate of FIG. 5 cut along section line 7-7 of FIG. 5;

FIG. 8 is an exploded perspective view of an occipital plate in accordance with another embodiment of the present disclosure;

FIG. 9 is a perspective view of the occipital plate of FIG. 1, illustrating use on a skull of a patient;

FIG. 10 is a side cross-sectional view of the occipital plate of FIG. 9 cut along section line 10-10 of FIG. 9; and FIG. 11 is an enlarged cross-sectional view of the indicated area of detail of FIG. 10.

DETAILED DESCRIPTION

The presently disclosed occipital plate will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during proper use. In addition, the term "cephalad" is used in this application to indicate a direction toward a patient's head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

With reference to FIGS. 1 and 2, an occipital plate in accordance with an embodiment of the present disclosure is generally shown as occipital plate 100. The occipital plate 100 includes a first portion 110 and a second portion 210. The first and second portions 110, 210 define a longitudinal axis "Y-Y" extending in cephalad and caudad directions. The occipital plate 100 is symmetric about the longitudinal axis "Y-Y." The occipital plate 100 may be formed of titanium alloy. Bone screws "B" (FIG. 9) and spinal rods "R" (FIG. 10) may be utilized to secure the occipital plate 100 to anatomical structures of the patient. Reference may be made to U.S. Pat. Nos. 9,295,494 and 9,339,307, the entire contents of each of which are incorporated herein by reference, for a detailed description of the construction of bone screws and spinal rods.

The first portion 110 defines bores 112 configured to receive respective bone screws. One of the bores 112 is positioned on the longitudinal axis "Y-Y" such that one of the bores 112 is centered and interposed between two adjacent bores 112. Each bore 112 is surrounded by a lip 114 formed of titanium alloy. The bone screws received in the bores 112 may include threads formed of a titanium alloy such as, e.g., Ti-6Al-4V. Alternatively, the bore 112 may include complementary threads for forming a secure attachment with the bone screw.

Each bore 112 defines an acute angle α with respect to an axis "O-O" (FIG. 6) orthogonal to a posterior surface 116 (FIG. 6) of the first portion 110. For example, the acute angle α may be in a range of about 10 and 30 degrees. In an embodiment, the acute angle α may be in a range of about 10 and 20 degrees. In another embodiment, the acute angle α may be about 15 degrees, i.e., each bore 112 may define an angle β of about 105 degrees with respect to the posterior surface 116. Defining the bore 112 at such an angle facilitates insertion of the bone screw during a surgical procedure. In particular, such a configuration enables the bone screw to accommodate e.g., the curvature of the skull "S" (FIG. 10), of the patient. In addition, the bone screw inserted at such an angle may further inhibit the bone screw from backing out of and separating from the first portion 110. Optionally, the first portion 110 may further define slots 150 dimensioned to receive a band (not shown), as described in U.S. Pat. No. 9,675,386, the entire contents of which are incorporated herein by reference, that is configured to further secure the occipital plate 100 to the anatomical structure of the patient. For example, adjacent bores 112 may be separated by the slot 150.

With reference now to FIGS. 3 and 4, the first portion 110 includes connector assemblies 130 disposed laterally outward of the bores 112. In particular, the connector assemblies 130 are disposed on opposing sides of the first portion 110. The first portion 110 is symmetric about the longitudinal axis "Y-Y." The first portion 110 further includes a mount 128 on each lateral side thereof. Each mount 128 defines a hole 127 therethrough. The mount 128 includes an engaging surface 128a protruding radially inward of the hole 127 for poly-axial engagement with the connector assembly 130.

With continued reference to FIG. 4, the connector assembly 130 is configured to securely support a spinal rod "R" (FIG. 11) therein. The connector assembly 130 is configured for poly-axial movement. In particular, each connector assembly 130 is movable through a cone in a range of about 10° and 30°. In an embodiment, each connector assembly 130 is movable through a cone in a range of about 20° and 30°. In another embodiment, each connector assembly 130 is movable through a cone of about 25°. The connector assembly 130 includes a housing 132 having a head portion 134 defining a slot 138 dimensioned to receive the spinal rod "R" therein, and a base portion 136 including threads 136a. The connector assembly 130 further includes a support 140 adjustably supporting the housing 132 on the mount 128, and a nut 146 configured to threadably engage the threads 136a on the base portion 136 of the housing 132 to secure the housing 132 to the mount 128. In particular, the support 140 has an annular configuration configured to receive the base portion 136 therethrough. The support 140 is slidably adjustable on the engaging surface 128a of the mount 128 to enable poly-axial movement of the housing 132 on the mount 128. The support 140 has an annular wall 142 defining diametrically opposing recesses 144 dimensioned to receive the spinal rod "R" therein. The adjustably mounted housing 132 may be secured to the mount 128 by threadably coupling the nut 146 to the base portion 136. In particular, poly-axial movement of the housing 132 with respect to the mount 128 is inhibited when a set screw is inserted and tightened in the housing 132 onto the spinal rod "R" seated on the support 140.

With reference now to FIG. 5, the occipital plate 100 further includes a second portion 210 that extends in a cephalad direction from the first portion 110. The second portion 210 includes a base portion 220 defining an axis "X-X" orthogonal to the longitudinal axis "Y-Y" (FIG. 4). The base portion 220 further defines bores 214 along the axis "X-X." One of the bores 214 is positioned along the longitudinal axis "Y-Y" and interposed between the other bores 214. Each bore 214 is surrounded by a lip 216 in a manner described with respect to the lip 114 (FIG. 1). In addition, the base portion 220 further defines slots 218 interposed between adjacent bores 214. The slot 218 may be configured to receive a band to further secure the occipital plate 100 to an anatomical structure of the patient. In addition, the base portion 220 may be cut or bent along the slot 218 to a suitable configuration in order to tailor the occipital plate 100 to the particular surgical procedure or the patient. The second portion 210 further includes an extension portion 240 extending in the cephalad direction from the base portion 220. The extension portion 240 defines a bore 222 disposed along the longitudinal axis "Y-Y." The bore 222 may be surrounded by a lip 224 in a manner described hereinabove with respect to the lip 114 (FIG. 1).

In use, the clinician initially prepares the occipital bone and the vertebrae. The clinician may form insertion holes in, e.g., osseous tissue, by preparing the surface with a burr or other like instrument and then an awl to start the hole. The clinician may secure bone anchors in vertebral bodies in order to secure spinal rods "R" (FIG. 10) to the vertebrae. Once the spinal rods "R" have been placed with the bone anchors, the clinician may perform posterior fixation of the occipital plate 100 to the occipital region of the spine. Based on the surgical procedure and the patient, the connector assemblies 130 (FIG. 7) may be rotated relative to the mount 128 in a poly-axial direction. The spinal rods "R" are placed in the respective connector assemblies 130 and are secured to the connector assemblies 130 by respective set screws (not shown). Thereafter, bone anchors are inserted through the bores 112 at an angle relative to a plane defined by the plate to secure the occipital plate 100 to the patient. Prior to securing the occipital plate 100 to the patient, the clinician may manipulate the second portion 210 by, for example, cutting or bending along, e.g., the slots 218, of the base portion 220. Thereafter, additional bone screws may be inserted through the bores 214 and/or 222 of the second portion 210, as needed, to secure the occipital plate 100 to the patient.

With reference now to FIG. 8, a connector assembly in accordance with another embodiment of the present disclosure is generally shown as a connector assembly 330. Parts of an occipital plate 300 including the connector assembly 330 substantially identical to the parts of the occipital plate 100 will not be described herein to avoid obscuring the present disclosure in unnecessary detail. The connector assembly 330 includes a housing 332, a support 140, a retaining ring 350, and a nut 346. While the connector assembly 130 (FIG. 1) is secured to the mount 128 by threadably coupling the base portion 136 of the housing 132 with the nut 146, the connector 330 includes the retaining ring 350 that is radially deflectable. The housing 332 includes a head portion 334 configured to receive a spinal rod "R", and a base portion 336 configured to extend through the support 140 and the hole 127. The base portion 336 defines a circular groove 336a dimensioned to receive the retaining ring 350 therein such that at least a portion of the retaining ring 350 extends radially outward when positioned in the groove 336a. The nut 346 defines a circular groove 346a configured to receive the portion of the retaining ring 350 extending radially outward from the circular groove 336a of the base portion 336a. Under such a configuration, the retaining ring 350 may be compressed and released in order to couple the nut 346 to the base portion 336 of the housing 332 when securing the housing 332 to the mount 128. The method of use of the occipital plate 300 including the connector assembly 330 is substantially identical to the use of the occipital plate 100, and thus, will not be described herein.

Persons skilled in the art will understand that the structures and methods specifically described herein and shown in the accompanying figures are non-limiting exemplary embodiments, and that the description, disclosure, and figures should be construed merely as exemplary of particular embodiments. For example, it is contemplated that the rod receiving portion of the housing may include a taper lock for locking the spinal rod relative to the housing, rather than a set screw design as shown. A suitable taper lock configuration may be adapted from the taper lock design shown in International Patent Application Publication No. WO 2009/055407, the entire contents of which are incorporated herein by reference. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical implant comprising:
   a first portion including:
      a body including a posterior surface, the body defining a first bore defining an acute angle with respect to a first axis that is orthogonal to the posterior surface; and
      a mount having an engaging surface;
   connector assemblies disposed on opposing lateral sides of the body, each connector assembly including a support slidably adjustable on the engaging surface of the mount to enable poly-axial movement; and
   a second portion including a base extending in a cephalad direction from the first portion, and an extension extending in the cephalad direction from the base, the base defining second bores configured to receive respective bone screws, the extension defining a third bore, the first bore of the body and the third bore of the extension defining a second axis, the second bores defined along a third axis orthogonal to the second axis.

2. The surgical implant according to claim 1, wherein the acute angle defined by the first bore is about 15 degrees.

3. The surgical implant according to claim 1, wherein at least one of the connector assemblies is configured for poly-axial movement.

4. The surgical implant according to claim 3, wherein the at least one of the connector assemblies is configured for poly-axial movement through a cone of about 25 degrees.

5. The surgical implant according to claim 1, wherein the mount defines a hole, the engaging surface protruding radially inward of the hole.

6. The surgical implant according to claim 5, wherein the connector assembly includes a housing defining a slot configured to receive a spinal rod, the support is configured to support the housing, and a nut configured to be coupled with the housing in order to couple the housing to the mount of the body.

7. The surgical implant according to claim 6, wherein the nut is configured to threadably engage the housing of the connector assembly.

8. The surgical implant according to claim 6, wherein the connector assembly further includes a radially deflectable retaining ring, at least a portion of the radially deflectable retaining ring configured to extend radially outward from a first circular groove defined in the housing.

9. The surgical implant according to claim 8, wherein the nut defines a second circular groove configured to receive the at least a portion of the radially deflectable retaining ring extending radially outward from the first circular groove of the housing.

10. The surgical implant according to claim 6, wherein the support has an annular configuration, the support defining diametrically opposing recesses configured to receive the spinal rod.

11. The surgical implant according to claim 1, wherein the body further defines fourth and fifth bores adjacent the first bore, at least one of the fourth or fifth bores defining an acute angle with respect to the first axis.

12. The surgical implant according to claim 1, wherein at least one of the first, fourth, or fifth bores is surrounded by a lip configured to deform.

13. The surgical implant according to claim 1, wherein second portion has an inverted T-shape.

14. The surgical implant according to claim 1, wherein first portion is symmetric about the second axis.

15. A method of surgery comprising:
   mounting a bone screw to a vertebra;
   securing a spinal rod to the bone screw;
   placing an occipital plate adjacent occipital region of a spine, the occipital plate including:
      a first portion including:
         a body defining first bore defining an acute angle with respect to a first axis that is orthogonal to a surface of the body;
         a mount having an engaging surface; and
         a connector assembly configured to receive the spinal rod, the connector assembly disposed on a lateral side of the first portion, the connector assembly including a support slidably adjustable on the engaging surface of the mount to enable poly-axial movement; and
      a second portion defining a second bore, the first and second bores arranged along a second axis;
   securing the spinal rod with the connector assembly; and
   securing the occipital plate to the occipital region of the spine.

16. The method according to claim 15, wherein securing the occipital plate includes mounting a bone screw to the occipital region of the spine through the first bore of the body.

17. The surgical implant according to claim 16, wherein securing the occipital plate includes mounting the bone screw to the occipital region of the spine at an angle of about 15 degrees with respect to the first axis.

18. The surgical implant according to claim 15, wherein securing the spinal rod with the connector assembly includes adjusting the connector assembly in a poly-axial direction relative to the body of the first portion.

19. The surgical implant according to claim 15, wherein securing the occipital plate includes mounting a bone screw to the occipital region of the spine through the second bore of the second portion.

* * * * *